(12) United States Patent
Netzel (10) Patent No.: US 6,180,350 B1
(45) Date of Patent: Jan. 30, 2001

(54) METHODS AND APPARATUS FOR THE PHOTO-ELECTROCHEMICAL DETECTION OF NUCLEIC ACID

(75) Inventor: Thomas Netzel, Atlanta, GA (US)

(73) Assignee: Georgia University Research Foundation Inc., Atlanta, GA (US)

( * ) Notice: Under 35 U.S.C. 154(b), the term of this patent shall be extended for 0 days.

(21) Appl. No.: 09/320,333

(22) Filed: May 26, 1999

Related U.S. Application Data (60) Provisional application No. 60/086,957, filed on May 26, 1998.

(51) Int. Cl.[7] ............................. C12Q 1/68; G01N 21/76
(52) U.S. Cl. .................................. 435/6; 435/6; 436/172
(58) Field of Search .................................. 435/6; 436/172

(56) References Cited

U.S. PATENT DOCUMENTS 5,591,578 * 1/1997 Meade et al. ............................. 435/6

OTHER PUBLICATIONS

Rawn, "Biochemistry"; Neil Patterson Publishers/Carolina Biological Supply Company, North Carolina 1989.*
Napier et al., "Probing Biomolecule Recognition with Electron Transfer: Electrochemical Sensors for DNA Hybridization", Bioconjugate Chem. 8, pp. 906–913, 1997.*
Brun et al., "Photochemistry of Intercalated Quaternary Diazaaromatic Salts" J. Am. Chem. Soc. 113, pp. 8153–8159, 1991.*
O'Connor et al., Influence of Adduct Sterochemistry and Hydrogen–Bonding Solvents on Photoinduced Charge Transfer in a Covalent Benzo[a]pyrene Diol epoxide—Nucleoside Adduct on Picosecond Time Scales, J. Phys. Chem. 98, pp. 9831–9839, 1994.*
Netzel et al., "Direct Observation of Photoinduced Electron Transfer in Pyrene–Labeled dU Nucleosides and Evidence for Protonated 2'-Deoxyuridine Anion, dU(H)* , as a Primary Electron Transfer Product", J. Phys. Chem. 99, pp. 17948–17955, 1995.*
Tarasiuk et al., "Molecular Determinats of Singlet Oxygen Binding by Anthraquinones in Relation to their Redox Cycling Activity", Anti–Cancer Drug Design 6, pp. 399–416, 1991.*

* cited by examiner

Primary Examiner—John S. Brusca
Assistant Examiner—Jeffrey S. Lundgren
(74) Attorney, Agent, or Firm—Anthony J. Janiuk (57) ABSTRACT

One embodiment of the present invention is a device and method for detecting the presence or absence of a signal nucleic acid. The device has comprising an electrode and a first nucleic acid covalently bound to the electrode. The first nucleic acid has two or more donor nucleotides capable of donating an electron. The donor nucleotides have a position in the first nucleic acid where one donor nucleotide is proximal to the electrode. The first nucleic acid has a modified nucleotide adjacent to one of the donor nucleotides. The modified nucleotide is capable of receiving an electron from said donor nucleotides upon photo-excitation and maintaining the electron for a first period of time when the first nucleic acid is unhybridized and a second period of time when the first nucleic acid is hybridized to the signal nucleic acid. The first and second periods are different. The electrode is in communication with the first nucleic acid to receive and donate electrons. The device further comprises a photon source for emitting photons onto the first nucleic acid. A charge monitor is in communication with the electrode for measuring the charge on the electrode or current flowing through the electrode as the first nucleic acid receives photons from the photon source which charge on said electrode is different in the presence of signal nucleic acid. The difference is indicative of the presence or absence of the signal nucleic acid.

19 Claims, 7 Drawing Sheets

METHODS AND APPARATUS FOR THE PHOTO-ELECTROCHEMICAL DETECTION OF NUCLEIC ACID

This application claims the benefit of U.S. Provisional Application No. 60/086,957, filed May 26, 1998

FIELD OF THE INVENTION

This application relates to compositions, methods and apparatus for the photo-electrochemical detection of nucleic acid of a defined sequence. In particular, one aspect of the invention features a device having an electrode, a first nucleic acid, a source for photons and a charge monitor. The first nucleic acid is covalently bound to the electrode with electron donor nucleotides proximal to the electrode and a modified nucleotide adjacent to the donor nucleotide. The modified nucleotide has a base with a functional group capable of receiving or donating electrons. The first nucleic acid donates or receives electrons from the electrode upon receiving photons. The rate at which the electrode receives or donates electrons with the first nucleic acid is different when the first nucleic acid is hybridized and when the first nucleic acid is unhybridized. The charge monitor measures the rate at which the electrode receives or donates electrons to determine the presence or absence of a second nucleic acid capable of forming a hybridization product with the first nucleic acid.

BACKGROUND OF THE INVENTION

The following definitions are provided to facilitate an understanding of the invention.

The term "target" or "target molecule", in a diagnostic sense, refers to a molecule of interest, i.e. the molecule whose presence one wants to know. This application uses the term "signal nucleic acid" to refer to the target, if such target is present in sufficient quanities to produce a measurable response. However, the term "signal nucleic acid" also refers to nucleic acid that may be generated in the presence of target. By way of example, without limitation, signal nucleic acid may be generated in the presence of non-nucleic acid targets or nucleic acid targets through nucleic acid amplification reactions such as polymerase chain reactions (PCR) and RNA-dependent RNA polymerase reactions, such as Q-Beta replicase.

Nucleic acid antibody reactions are characterized by processes which are called SELEX (NexStar Pharmaceuticals, Inc., Boulder CO). These processes describe the manner in which nucleic acids may be selected for affinity to non-nucleic acid targets, such as proteins and other molecules of interest. The selected nucleic acids can be used as ligands for affinity reactions in the manner similar to antibodies.

Nucleic acid hybridization reactions are based on the affinity exhibited by complementary strands of nucleic acid. Nucleic acid target molecules can be identified by the binding of such target to a complementary ligand nucleic acid.

Assays based on nucleic acid antibodies and nucleic acid hybridization tend to be time consuming and complex. There exists a need for photo-electrochemical detection of signal nucleic acid.

SUMMARY OF THE INVENTION

This application relates to compositions, methods and apparatus for the photo-electrochemical detection of nucleic acid of a defined sequence. One embodiment of the present invention is a device for detecting the presence or absence of a signal nucleic acid. The device has comprising an electrode and a first nucleic acid covalently bound to the electrode. The first nucleic acid has two or more donor nucleotides capable of donating an electron. The donor nucleosides have a position in the first nucleic acid where one donor nucleotide is proximal to the electrode. The first nucleic acid has a modified nucleotide adjacent to one of the donor nucleosides. The modified nucleotide is capable of receiving an electron from said donor nucleotides upon photo-excitation and maintaining the electron for a first period of time when the first nucleic acid is unhybridized and a second period of time when the first nucleic acid is hybridized to the signal nucleic acid. The first and second periods are different. The electrode is in communication with the first nucleic acid to receive and donate electrons. The device further comprises a photon source for emitting photons onto the first nucleic acid. A charge monitor is in communication with the electrode for measuring the charge on the electrode or current flowing through the electrode as the first nucleic acid receives photons from the photon source which charge on said electrode or current is different in the presence of signal nucleic acid. The difference is indicative of the presence or absence of the signal nucleic acid.

Preferably, the modified nucleotide comprises a base and a functional group, and the donor nucleotides are more easily oxidized than the base of the modified nucleotide. Of the bases which comprise the first nucleic acid, guanine is more easily oxidized than adenine. Adenine is more easily oxidized than uracil, thymine, and cytosine. A preferred two or more donor nucleotides comprise three or more guanosine nucleotides.

Preferably, the modified nucleotide comprises a base selected from the group of bases consisting of guanine, adenine, uracil, thymine and cytosine having a functional group capable of receiving an electron from said base upon the modified nucleotide receiving photon energy. And, preferably, the functional group is photo-reactive.

A preferred functional group is selected from the group consisting of anthraquinone, naphthalene, phenanthrene, pterins, pyrene, quinidine, quinolone and derivatives thereof. Particularly preferred modified nucleoside are anthraquinoneacetyl-N(C6)-2'-deoxyadenine and N6-(anthraquinone-2-carbonyl)-2'-deoxyadenosine.

Preferably, the first nucleic acid is deoxyribose nucleic acid (DNA) and the signal nucleic acid is selected from the group of nucleic acids consisting of RNA replicase template nucleic acid, ribosomal RNA, messenger RNA, and target DNA and RNA nucleic acid.

Preferably, the photon source is pulsed and said charge monitor measures the difference between said first and second periods. The charge monitor is preferably phase locked with the photon source. This allows signal averaging at kilohertz or greater frequencies. A preferred photon source is a YAG laser or xenon flash light. The difference in the first and second periods can be detected as current through conventional equipment.

The electrode is preferably paired with a opposing electrode and the charge monitor measures current flowing between the electrodes as the electrodes are immersed in a sample potentially containing the signal nucleic acid.

A further embodiment of the present invention is a method for detecting the presence or absence of a signal nucleic acid. The method comprises the steps of providing a device having an electrode and a first nucleic acid covalently bound to the electrode acid to receive and donate electrons. The first nucleic acid has two or more donor nucleotides capable of donating an electron. The donor nucleotides have a position in the first nucleic acid where one donor nucleotide is proximal to the electrode. The first nucleic acid has a modified nucleoside adjacent to one of the donor nucleotides. The modified nucleotide is capable of receiving an electron from the donor nucleotides upon photo-excitation and maintaining the electron for a first period of time when the first nucleic acid is unhybridized and a second period of time when the first nucleic acid is hybridized to the signal nucleic acid. The first and second periods are different. The device further has a photon source for emitting photons on the first nucleic acid and, a charge monitor in communication with the electrode. The charge monitor measure the charge on the electrode or current flowing through the electrode as the first nucleic acid receives photons from the photon source. The charge on the electrode or current through the electrode is different in the presence of signal nucleic acid. The difference is indicative of the presence or absence of the signal nucleic acid. The method further comprises the step of contacting the first nucleic acid with a sample potentially containing the signal nucleic acid under conditions in which the signal nucleic acid will hybridize with the first nucleic acid. And, the method includes the step of generating photons from the photon source; and measuring the charge on the electrode or current with the charge monitor during the generation of photons, in the presence of sample and comparing such charge to at least one value selected from the group consisting of a control value, or a value selected over time spanning the first and second periods. The difference is indicative of the presence or absence of the signal nucleic acid.

Other features and advantages of the present invention will be apparent from the following detailed description and the drawings, which, by way of example, demonstrate preferred embodiments of the present invention and the principles thereof, and the best mode to apply these principles.

Detailed Description

To facilitate a discussion of the present invention reference will be made to the accompanying drawings. This application relates to compositions, methods and apparatus for the photo-electrochemical detection of nucleic acid of a defined sequence. The nucleic acid of defined sequence, for the purpose of the present discussion, will be the signal nucleic acid.

Figure 1A:
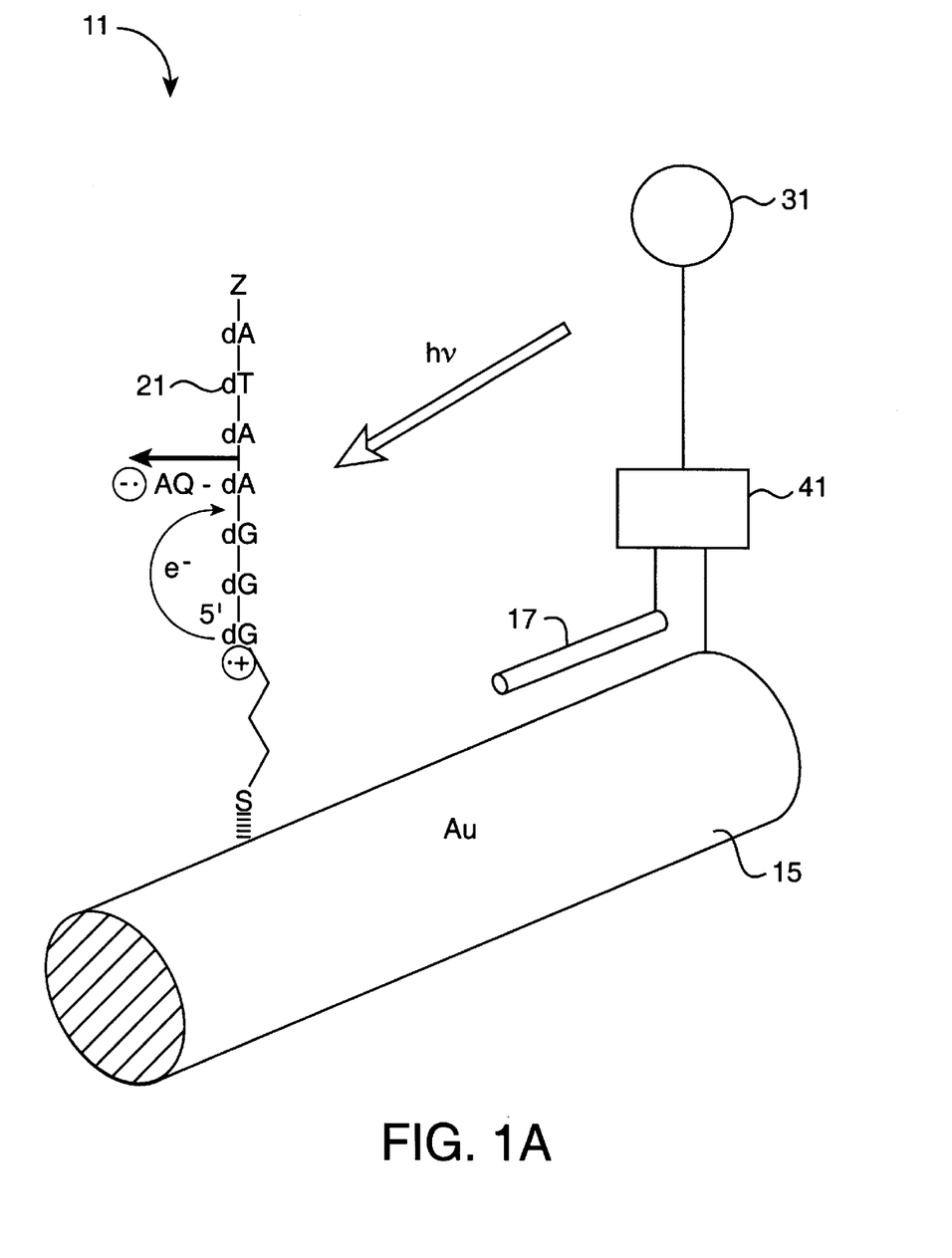
FIG. 1A depicts a device incorporating features of the present invention.

Turning now to FIG. 1A, an embodiment of the present invention, a device for detecting the presence or absence of a signal nucleic acid, generally referred to by the numeral 11, is illustrated in schematic form. The device 11 has a first electrode 15 and a second electrode 17. Preferably, the first electrode has a gold surface to allow covalent binding of a first nucleic acid. The process of binding such first nucleic acid to a gold substrate is well-known. An interferometric sensor (not shown) may substituted for the electrode 15, in a manner known to individuals skilled in the art.

A first nucleic acid 21 is covalently bound to the first electrode 15. The letter "Z" represents sequences of nucleic acid which are complementary to the signal nucleic acid. The first nucleic acid 21 has two or more donor nucleotides capable of donating an electron. FIG. 1A depicts three donor nucleotides, the guanosines most proximal to the electrode 15. The donor nucleosides have a position in said first nucleic acid where one donor nucleotide is proximal to the electrode 15.

Figure 2A:
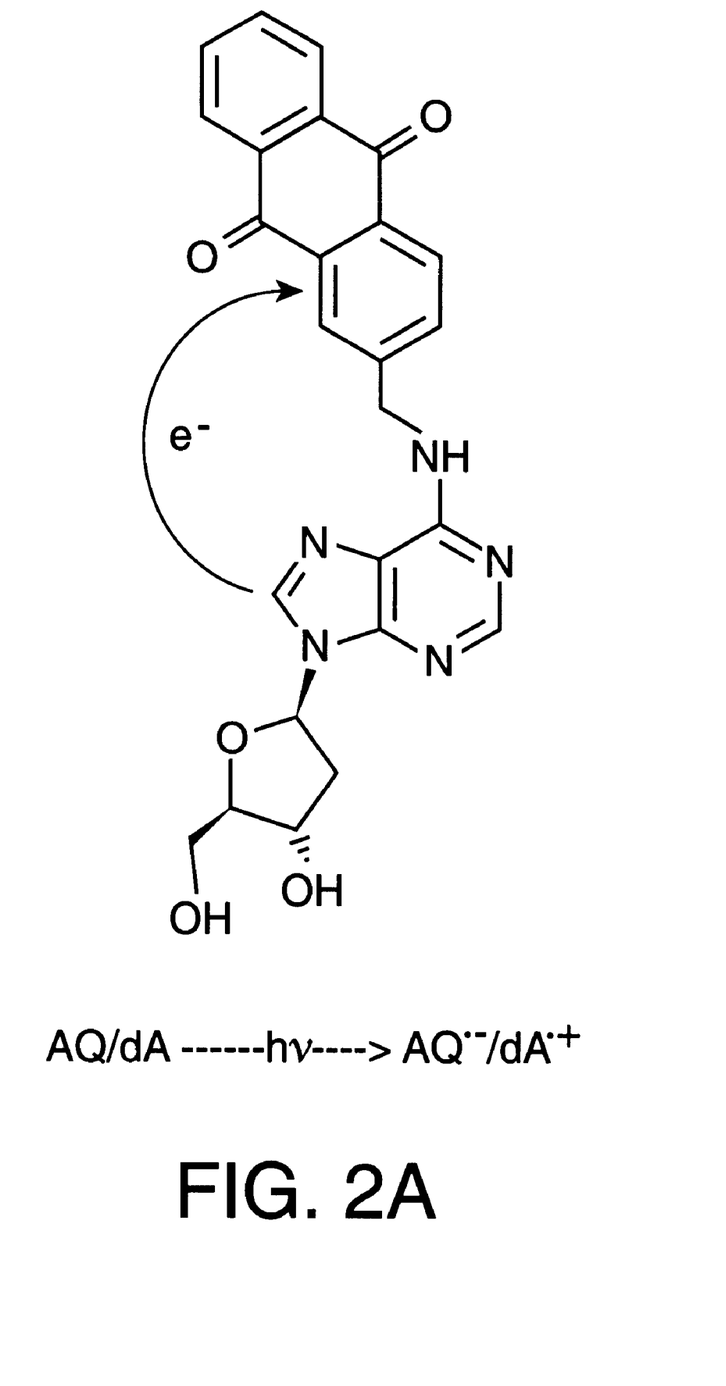
FIG. 2A depicts a preferred modified nucleotide.

The first nucleic acid 21 has a modified nucleotide, "AQ-dA", adjacent to one of the donor nucleosides. Preferably, the functional group is photo-reactive. A preferred functional group is selected from the group consisting of anthraquinone, naphthalene, phenanthrene, pterins, pyrene, quinidine, quinolone and derivatives thereof. A preferred modified nucleotide is depicted in FIG. 2A, anthraquinoeacetyl-N(C6)-2'-deoxyadenosine. This nucleoside can be synthesized by individuals skilled in the art of synthetic chemistry.

Figure 2B:
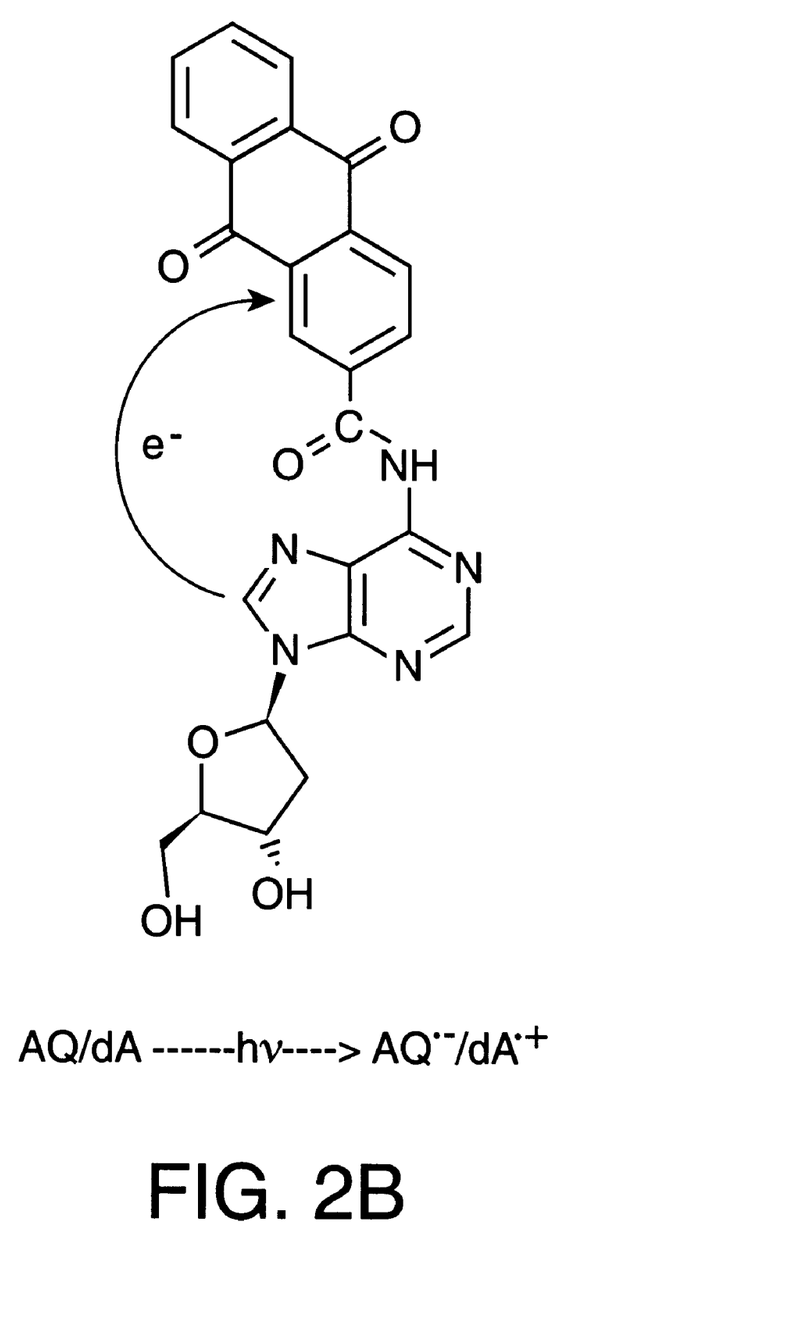
FIG. 2B depicts a preferred modified nucleotide.

A further preferred modified nucleotide is depicted in FIG. 2B, N6-(anthraquinone2-carbonyl)-2'-deoxyadenosine. This nucleoside can also be synthesized by individuals skilled in the art of synthetic chemistry.

Figure 3A:
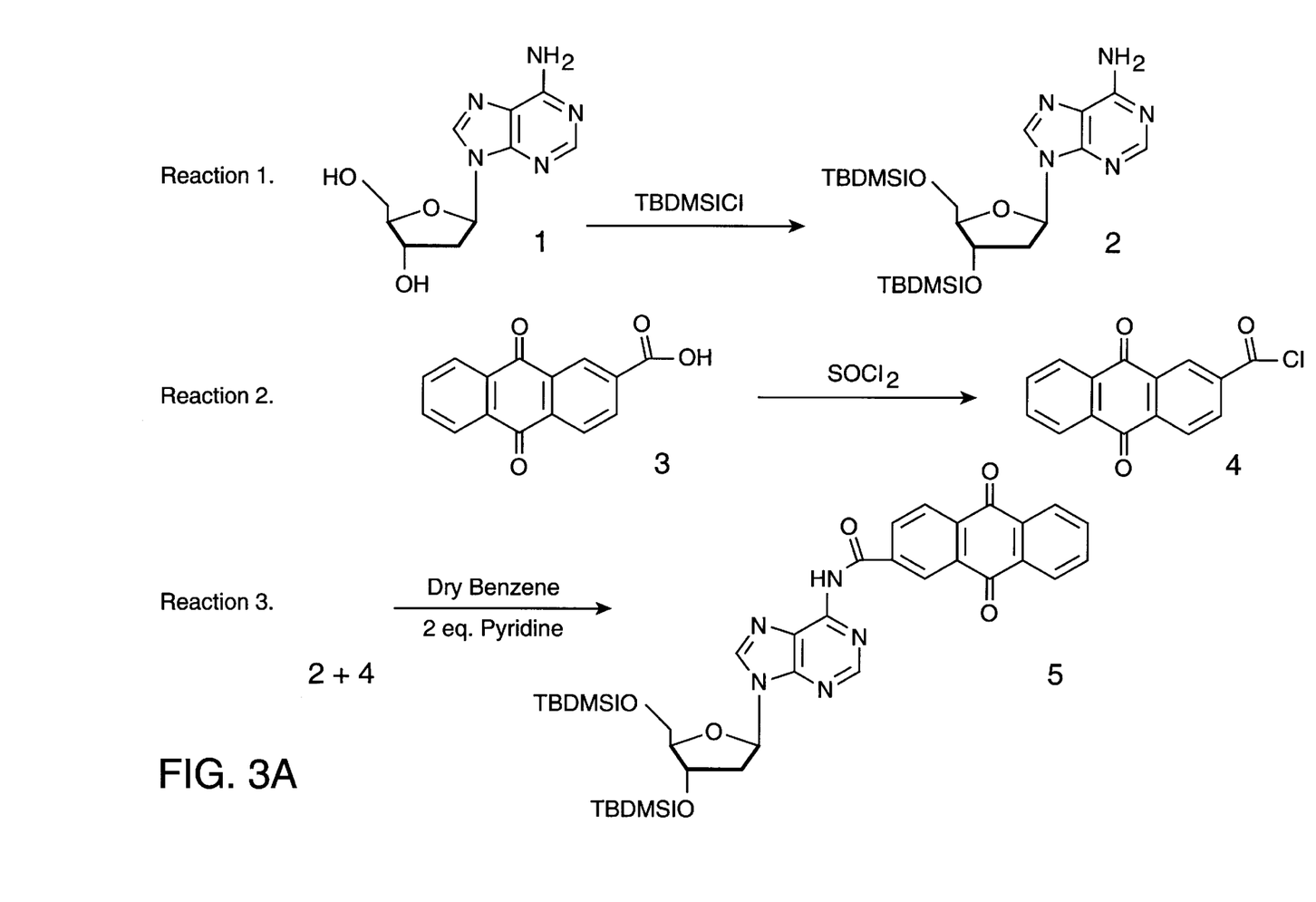
FIGS. 3A and 3B depicts a reaction scheme for making a preferred nucleotide.
Figure 3B:
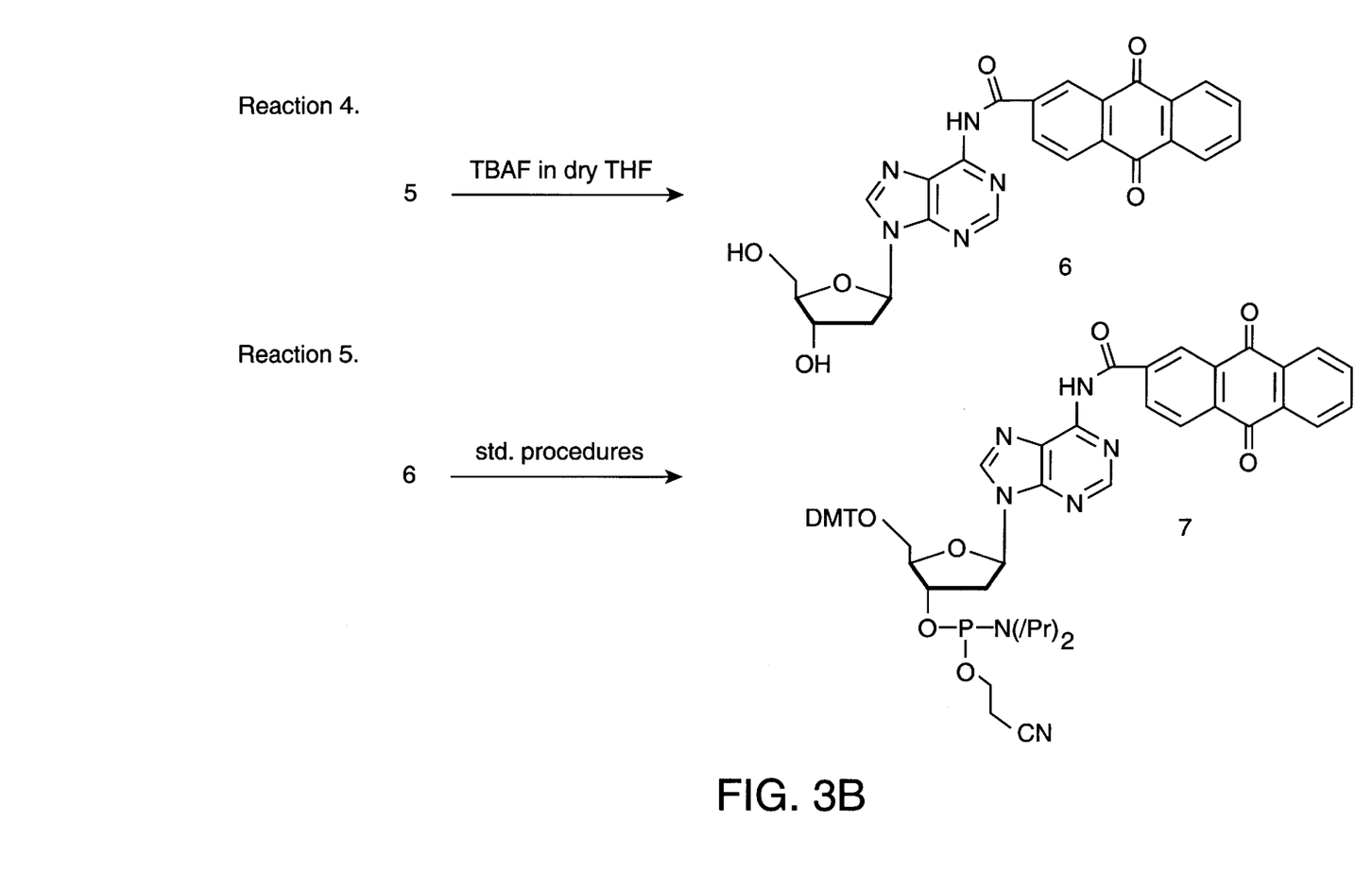

A scheme for the synthesis of this nucleotide is illustrated in FIGS. 3A and 3B. Briefly, in Reaction 1, commercially available 2'-deoxyadenosine 1 is reacted with t-butyldimethylsilyl chloride (TBDMSiCl) to protect the 5'-and 3'-O-positions on the sugar with an easily removable t-butyldimethylsilyl group (TBDMSi) and produce 2. In Reaction 2, commercially available anthraquinone-2-carboylic acid is reacted with sulfonyl chloride to make anthraquinone-2-carbonyl chloride 4. In Reaction 3, compounds 2 and 4 are reacted with each other in the presence of a weak base such as pyridine in a dry aromatic solvent such as benzene to produce 5, N6-(anthrquinone-2-carbonyl)-3', 5'-di(t-butyldimethylsilyl)-2'-deoxyadenosine. In Reaction 4, the 3', 5'-TBDMSi groups are removed from 5 by reaction with tetrabutylamonium fluoride (TBAF) in dry tetrahydrofuran (THF) to produce the nucleoside 6, N6-(anthraquinone-2carbonyl)-2'-deoxyadenosine. In Reaction 5, compound 7, the 5'-O-dimethyloxytrityl-3'-O-(2-cyanoethoxy)-N,N-diisopropylaminophosporamidite of 6 using standard procedures for making phosporamidite reagents for use in automated DNA synthesizers. First, the 5'-O position is protected with the dimethoxytrityl (DMT) group using 4, 4'-dimethoxytrityl chloride in dry pyridine. And, second, the 2'-O-position is reacted with 2-cyanoethoxy-N,N-diisoprpylaminochlorophosphine in an anhydrous mixture of N,N-diisopropylethylamine and dichloromethane.

Returning now to FIG. 1A, the modified nucleotide is capable of receiving an electron from the donor nucleotides upon photo-excitation and maintaining the electron for a first period of time when the first nucleic acid 21 is unhybridized and a second period of time when said first nucleic acid 21 is hybridized to the signal nucleic acid.

Figure 1B:
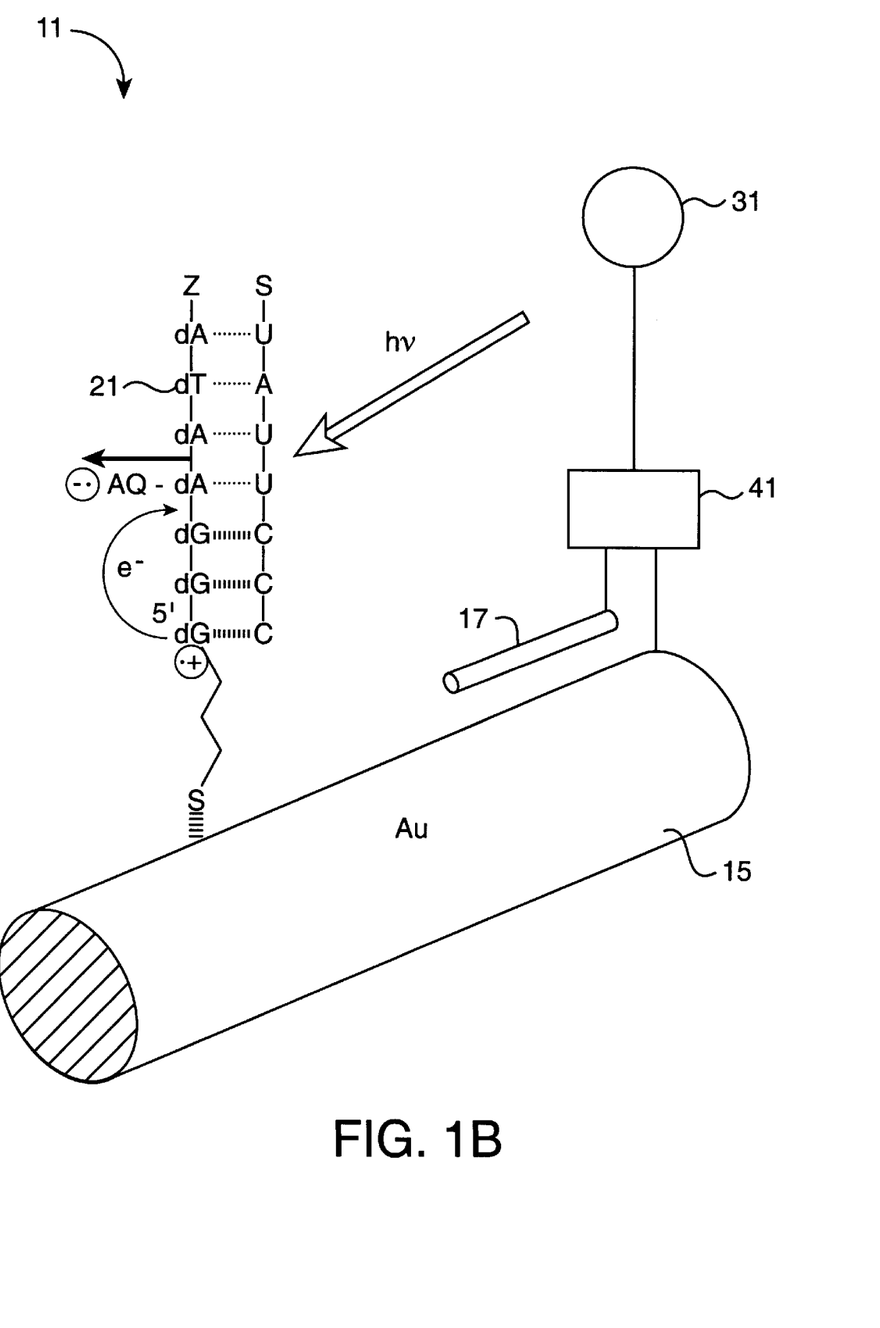
FIG. 1B depicts a device incorporating features of the present invention in the presence of a signal nucleic acid.

FIG. 1B depicts the first nucleic acid hybridized to the signal nucleic acid 23. The letter "S" denotes nucleotides in a sequence complementary to the first nucleic acid sequences "Z".

Figure 4:
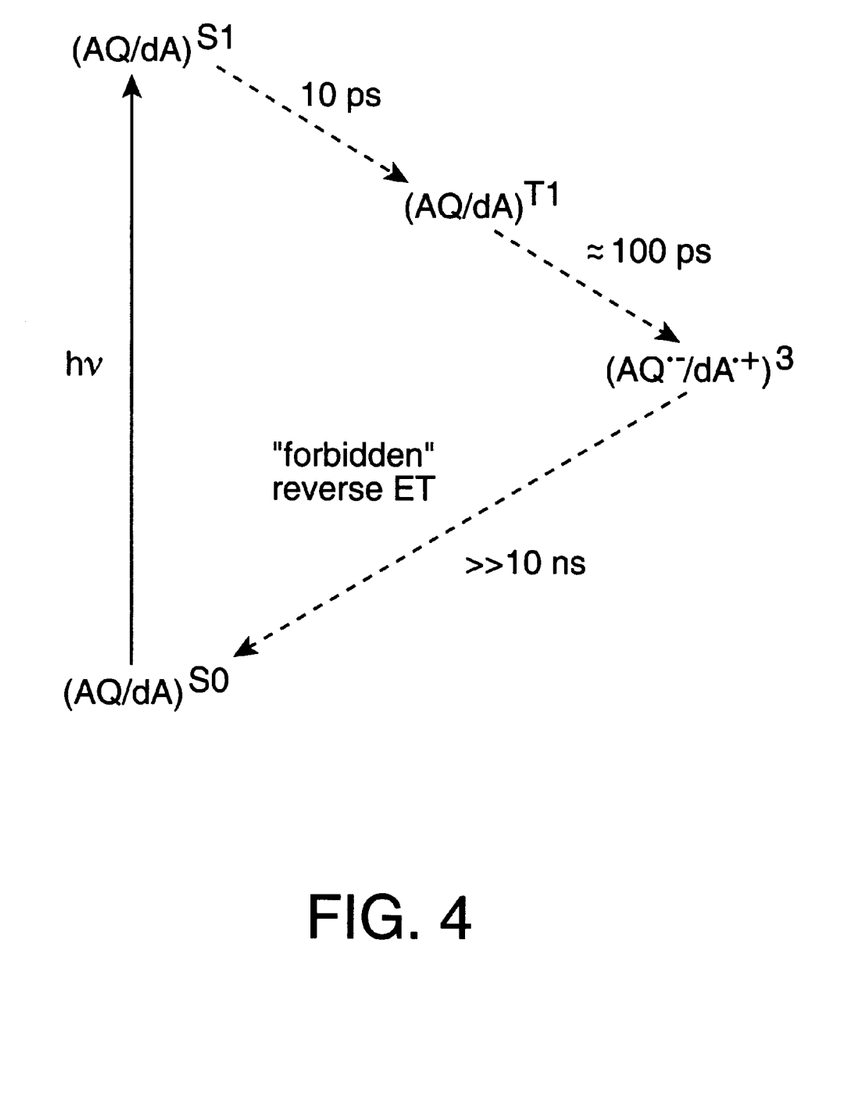
FIG. 4 depicts a forbidden reverse electron transfer giving rise to the different current or charge on the electrode in a hybridized versus unhybridized state.

The first and second periods are different and can be measured. The basis for the difference in the periods is illustrated in FIG. 4. FIG. 4 illustrates the excitation of the modified nucleotide, AQ-dG. The modified nucleotide moves quickly from a low energy state, S0, to a higher state, S1. Within picoseconds, an ionic form of the nucleotide is formed, which can not readily move to the original state because the reverse electron transfer is spin prohibited. To return to the original state, requires a period of 10 nanoseconds. However, in the presence of the signal nucleic acid 23, the reverse electron transfer is altered. As a single strand of DNA, the the modified nucleotide and the closest donor nucleotide of the first nucleic acid can combine rapidly allowing subsequent oxidation of donor nucleotides. However, the donor nucleotide closest to the modified nucleotide is most favored in the single stranded state. In the double stranded state, in the presence of the signal nucleic acid, the oxidation of the donor nucleotide most distant to the modified nucleotide, the donor nucleotide proximal to the electrode 15, is favored. Since it is further away, it will have a longer lifetime. The electrode 15 is in communication with said first nucleic acid 21 to receive and donate electrons.

The device further comprises a photon source 31 for emitting photons onto the first nucleic acid 21. Preferably, the photon source 31 is pulsed. A preferred photon source 31 is a YAG laser or xenon flash light. The difference in the first and second periods can be detected as current through conventional equipment.

The device further comprises a charge monitor 41. The charge monitor 41 measures the difference between said first and second periods. The charge monitor is preferably phase-locked with the photon source 31. This allows signal averaging at kilohertz or greater frequencies.

A charge monitor 41 is in communication with the electrode 15 for measuring the charge on said electrode or current flowing through the electrode 15 to electrode 17 as the first nucleic acid receives photons from the photon source. The charge on said electrode or the current flowing through the electrode 15 is different in the presence of signal nucleic acid 23. The difference is indicative of the presence or absence of the signal nucleic acid 23. A preferred charge monitor is sold by BAS as cyclic voltrametric equipment.

Preferably, the first nucleic acid is deoxyribose nucleic acid (DNA) and the signal nucleic acid is selected from the group of nucleic acids consisting of RNA replicase template nucleic acid, ribosomal RNA, messenger RNA, and target DNA and RNA nucleic acid. The signal nucleic acid is placed in a suitable collection vessel (not shown for the purpose of clarity) which vessel contains the electrodes 15 and 17. The charge monitor 41 measures current flowing between the electrodes 15 and 17 as the electrodes are immersed in a sample potentially containing the signal nucleic acid.

A further embodiment of the present invention is a method for detecting the presence or absence of a signal nucleic acid. The method is discussed herein as the operation of the device 11. Thus, the method comprises the steps of providing a device 11 having an electrode 15 and a first nucleic acid 21 covalently bound to the electrode 21 to receive and donate electrons. The first nucleic acid 21 has two or more donor nucleotides capable of donating an electron. The donor nucleotides have a position in the first nucleic acid where one donor nucleotide is proximal to said electrode 15. The first nucleic acid has a modified nucleoside adjacent to one of the donor nucleotides. The modified nucleotide capable of receiving an electron from the donor nucleotides upon photo-excitation and maintaining the electron for a first period of time when said first nucleic acid is unhybridized and a second period of time when said first nucleic acid is hybridized to the signal nucleic acid. The first and second periods are different. The device further has a photon source 31 for emitting photons on said first nucleic acid 21 and, a charge monitor 41 in communication with said electrode 15. The charge monitor 41 measures the charge on the electrode 15 or current flowing through the electrode 15 as said first nucleic acid 21 receives photons from the photon source 31. The charge on the electrode 15 or current through the electrode 15 is different in the presence of signal nucleic acid 23. The difference is indicative of the presence or absence of said signal nucleic acid 23. The method further comprises the step of contacting the first nucleic acid 21 with a sample potentially containing said signal nucleic acid 23 under conditions in which the signal nucleic acid 23 will hybridize with the first nucleic acid 21. And, the method includes the step of generating photons from the photon source 31; and measuring the charge on the electrode 15 or current with the charge monitor 41 during the generation of photons, in the presence of sample and comparing such charge to at least one value selected from the group consisting of a control value, or a value selected over time spanning the first and second periods. The difference is indicative of the presence or absence of the signal nucleic acid 23.

While the preferred embodiments have been illustrated and described, it is understood that the present invention is capable of variation and modification and, therefore, should not be limited to the precise details set forth, but should include such changes and alterations that fall within the purview of the following claims.

What is claimed is:

1. A device for detecting the presence or absence of a signal nucleic acid comprising:
   a) an electrode or interferometric sensor;
   b) a first nucleic acid covalently bound to said electrode or interferometric sensor, said first nucleic acid having two or more donor nucleotides capable of donating an electron, said donor nucleotides having a position in said first nucleic acid where one donor nucleotide is proximal to said electrode or interferometric sensor, said first nucleic acid having a modified nucleotide adjacent to one of said donor nucleotides, said modified nucleotide capable of receiving said electron from said donor nucleotides upon photo-excitation and maintaining said electron for a first period of time when said first nucleic acid is unhybridized and a second period of time when said first nucleic acid is hybridized to said signal nucleic acid, said first and second periods being different, said electrode or interferometric sensor in communication with said first nucleic acid to receive and donate electrons;
   c) a photon source for emitting photons on said first nucleic acid; and,
   d) a charge monitor in communication with said electrode or interferometric sensor for measuring the charge on said electrode or interferometric sensor as said first nucleic acid receives photons from said photon source which charge on said electrode is different in the presence of signal nucleic acid and said difference is indicative of the presence or absence of said signal nucleic acid.

2. The device of claim 1 wherein said modified nucleotide comprises a base and a functional group, and said donor nucleotides are more easily oxidized than said base of said modified nucleotide.

3. The device of claim 1 wherein said modified nucleotide comprises a base selected from the group of bases consisting of guanine, adenine, uracil, thymine and cytosine having a functional group capable of receiving an electron from said base upon said modified nucleotide receiving photon energy.

4. The device of claim 3 wherein said functional group is photo-reactive.

5. The device of claim 4 wherein said functional group is selected from the group consisting of anthraquinone, quinidine, and quinolone.

6. The device of claim 4 wherein said modified nucleotide is anthraquinoneacetyl-N(C6)-2'-adenosine or N6-(anthraquinone-2-carbonyl)-2'-deoxyadenosine.

7. The device of claim 1 wherein said first nucleic acid is deoxyribose nucleic acid (DNA).

8. The device of claim 1 wherein said signal nucleic acid is selected from the group of nucleic acids consisting of RNA replicase template nucleic acid, ribosomal RNA, messenger RNA, and target DNA and RNA nucleic acid.

9. The device of claim 1 wherein said photon source is pulsed and said charge monitor measures the difference between said first and second periods.

10. A method for detecting the presence or absence of a signal nucleic acid comprising the following steps:
a) providing a device comprising the following:
  i) an electrode or interferometric sensor;
  ii) a first nucleic acid covalently bound to said electrode or interferometric sensor, said first nucleic acid having two or more donor nucleotides capable of donating an electron, said donor nucleotides having a position in said first nucleic acid where one donor nucleotide is proximal to said electrode or interferometric sensor, said first nucleic acid having a modified nucleotide adjacent to one of said donor nucleotides, said modified nucleotide capable of receiving said electron from said donor nucleotides upon photo-excitation and maintaining said electron for a first period of time when said first nucleic acid is unhybridized and a second period of time when said first nucleic acid is hybridized to said signal nucleic acid, said first and second periods being different;
  iii) a photon source for emitting photons on said first nucleic acid; and,
  iv) a charge monitor in communication with said electrode or interferometric sensor for measuring the charge on said electrode or interferometric sensor as said first nucleic acid receives photons from said photon source which charge on said electrode or interferometric sensor is different in the presence of signal nucleic acid and said difference is indicative of the presence or absence of said signal nucleic acid;
b) contacting said first nucleic acid with a sample potentially containing said signal nucleic acid under conditions in which said signal nucleic acid will hybridize with said first nucleic acid, said electrode or interferometric sensor in communication with said first nucleic acid to receive and donate electrons;
c) generating photons from said photon source; and,
d) measuring the charge on said electrode with said charge monitor during the generation of photons, in the presence of sample and comparing such charge to at least one value selected from the group consisting of a control value, or a value selected over time spanning the first and second periods, the difference indicative of the presence or absence of the signal nucleic acid.

11. The method of claim 10 wherein said modified nucleotide comprises a base and a functional group, and said donor nucleotides are more easily oxidized than said base of said modified nucleotide.

12. The method of claim 10 wherein said modified nucleotide comprises a base selected from the group of bases consisting of guanine, adenine, uracil, thymine and cytosine having a functional group capable of receiving an electron from said base upon said modified nucleotide receiving photon energy.

13. The method of claim 10 wherein said functional group is photo-reactive.

14. The method of claim 13 wherein said functional group is selected from the group consisting of anthraquinone, quinidine, and quinolone.

15. The method of claim 14 wherein said modified nucleotide is anthraquinoneacetyl-N(C6)-2'-adenosine or N6-(anthraquinone-2-carbonyl)-2'-deoxyadenosine.

16. The method of claim 11 wherein said first nucleic acid is deoxyribose nucleic acid (DNA).

17. The method of claim 11 wherein said signal nucleic acid is selected from the group of nucleic acids consisting of RNA replicase template nucleic acid, ribosomal RNA, messenger RNA, and target DNA and RNA nucleic acid.

18. The method of claim 11 wherein said signal nucleic acid is selected from the group of nucleic acids consisting of RNA replicase template nucleic acid, ribosomal RNA, messenger RNA, and target DNA and RNA nucleic acid.

19. The method of claim 11 wherein said photon source is pulsed and said charge monitor measures the difference between said first and second periods.

* * * * *